United States Patent
Netherly et al.

[11] Patent Number: 5,827,184
[45] Date of Patent: Oct. 27, 1998

[54] SELF-PACKAGING BIOELECTRODES

[75] Inventors: Samuel G. Netherly, Afton, Minn.; Scott A. Burton, Essex Junction, Vt.

[73] Assignee: Minnesota Mining And Manufacturing Company, St. Paul, Minn.

[21] Appl. No.: 580,654

[22] Filed: Dec. 29, 1995

[51] Int. Cl.$^6$ .................................................... A61B 5/04
[52] U.S. Cl. ......................... 600/372; 600/391; 600/395; 607/152
[58] Field of Search .................................. 128/639–644; 607/152; 229/314, 316; 383/205, 207; 600/372, 382, 384, 391–397

[56] References Cited

U.S. PATENT DOCUMENTS

| | | | |
|---|---|---|---|
| Re. 24,906 | 12/1960 | Ulrich | 206/59 |
| Re. 33,353 | 9/1990 | Heinecke | 428/40 |
| 2,973,826 | 3/1961 | Barnhart | 182/91 |
| 3,389,827 | 6/1968 | Abere et al. | 220/53 |
| 4,112,213 | 9/1978 | Waldman | 526/279 |
| 4,248,247 | 2/1981 | Ware et al. | 607/152 |
| 4,310,509 | 1/1982 | Berglund et al. | 424/28 |
| 4,323,557 | 4/1982 | Rosso et al. | 424/28 |
| 4,353,373 | 10/1982 | Sessions et al. | 128/641 |
| 4,365,634 | 12/1982 | Bare et al. | 128/640 |
| 4,393,584 | 7/1983 | Bare et al. | 29/877 |
| 4,524,087 | 6/1985 | Engel | 427/2 |
| 4,539,996 | 9/1985 | Engel | 128/640 |
| 4,732,808 | 3/1988 | Krampe et al. | 428/355 |
| 4,848,353 | 7/1989 | Engel | 128/640 |
| 4,917,928 | 4/1990 | Heinecke | 428/41 |
| 4,917,929 | 4/1990 | Heinecke | 428/41 |
| 5,104,036 | 4/1992 | Rutkowski et al. | 229/316 |
| 5,133,356 | 7/1992 | Bryan et al. | 128/640 |
| 5,215,087 | 6/1993 | Anderson et al. | 128/640 |
| 5,225,473 | 7/1993 | Duan | 524/388 |
| 5,276,079 | 1/1994 | Duan et al. | 524/386 |
| 5,320,598 | 6/1994 | Haak et al. | 607/152 |
| 5,338,490 | 8/1994 | Dietz et al. | 252/500 |
| 5,362,420 | 11/1994 | Itoh et al. | 252/500 |
| 5,385,679 | 1/1995 | Uy et al. | 252/500 |
| 5,402,884 | 4/1995 | Gilman et al. | 206/328 |

FOREIGN PATENT DOCUMENTS

| | | | |
|---|---|---|---|
| 0 051 935 A2 | 5/1982 | European Pat. Off. | A61F 13/02 |
| WO 94/12585 | 6/1994 | WIPO | C09J 171/00 |
| WO 94/26950 | 11/1994 | WIPO | C23C 14/20 |
| WO 95/20350 | 8/1995 | WIPO | A61B 5/0408 |
| WO 95/20634 | 8/1995 | WIPO | C09J 7/02 |

*Primary Examiner*—Lee S. Cohen
*Assistant Examiner*—David M. Ruddy
*Attorney, Agent, or Firm*—Gary L. Griswold; Walter N. Kirn; John H. Hornickel

[57] ABSTRACT

A bioelectrode having a backing, a conductive layer adjacent to the backing, and a layer of conductive adhesive adjacent to the conductive layer. This bioelectrode is designed to have two special configurations. It is originally manufactured in its first configuration wherein the backing forms a sealed protective enclosure for the layer of conductive adhesive. When a physician is ready to apply the electrode to a patient, the electrode is readily converted to its second configuration wherein the layer of conductive adhesive is exposed for contacting and adhering the bioelectrode to the body of the patient.

14 Claims, 3 Drawing Sheets

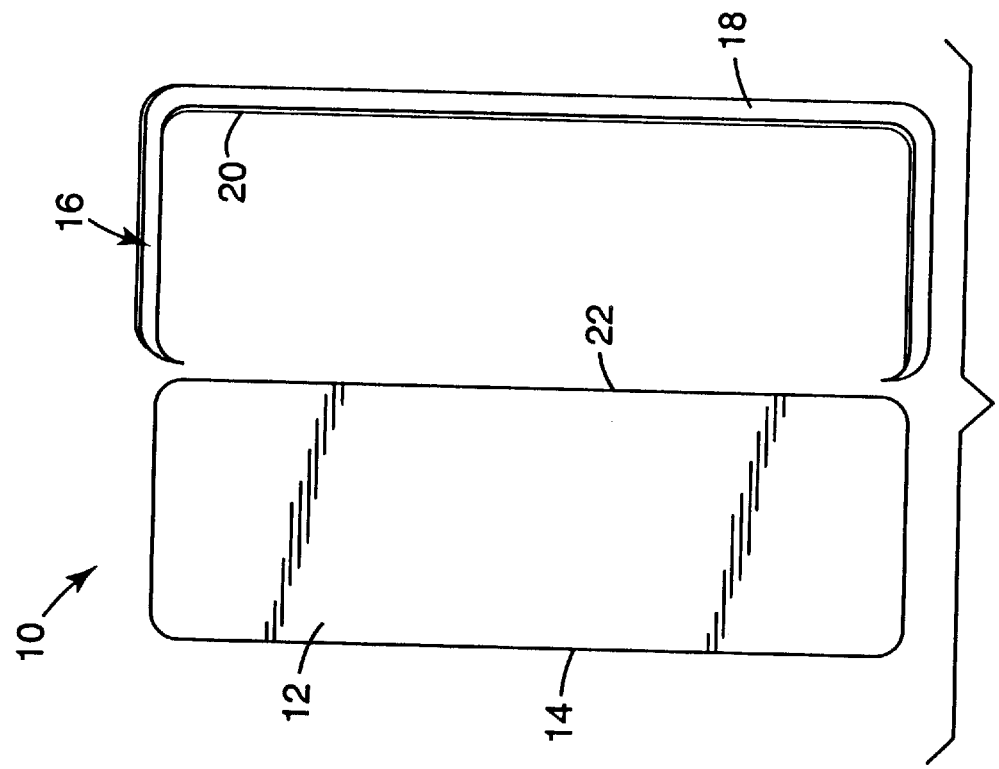
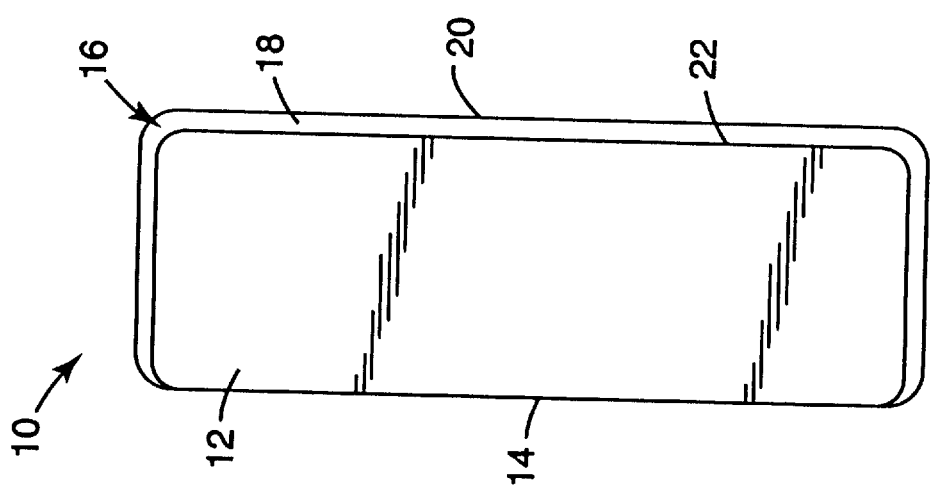

SELF-PACKAGING BIOELECTRODES

TECHNICAL FIELD

The present invention relates generally to bioelectrodes, and more particularly to bioelectrodes which minimize packaging waste.

BACKGROUND

In order to minimize the risk of spreading infection within a hospital, many products intended for direct contact with a patient are disposed of after a single use. One problem with using such disposable products is the volume of waste generated, not only by the product itself, but also by the packaging material the product may require. A second problem is the cost of such packaging; the consumer must eventually pay both for the packaging material itself in its disposal.

These two problems are particularly acute in the field of packaging for bioelectrodes. Bioelectrodes are used in great numbers, and that volume of usage increases their percentage contribution to a hospital's waste stream. Further, packaging which adequately protects bioelectrodes is particularly bulky and expensive. This is because whether a bioelectrode is intended to sense the body's natural electrical currents for diagnosis or to deliver electrical current to the body for therapy, a layer of a specialized body-contacting substance is needed to transfer the current. In recent years, the substance has usually been a soft, conductive adhesive which can fill the dual role of transferring the current and of adhering the electrode to the body. Many of the best known conductive adhesives are "hydrophilic", tending to have water or to absorb water. The packaging for bioelectrodes must therefore protect the conductive adhesive from physical damage or contamination, and also from losing its water content through drying out. It is clear that the art requires a bioelectrode designed to minimize the volume of packaging material required.

SUMMARY OF THE INVENTION

The present invention solves the problems discussed above by providing bioelectrodes with an outer portion that enables them to serve largely as their own packaging. The outer portions of these bioelectrodes are resistant to both impact and dry-out. They can be configured in one way to protect the physically delicate conductive adhesive during shipping and handling, and in another way to expose the conductive adhesive to transfer current to or from the body during use.

The invention has at least two aspects. In the first aspect, the invention provides a bioelectrode having a backing, a conductive layer contacting the backing, and a layer of conductive adhesive contacting the conductive layer. This bioelectrode is designed to have two configurations. It is originally manufactured in its first or "closed" configuration wherein the backing forms a sealed protective enclosure for the layer of conductive adhesive. When a physician is ready to apply the electrode to a patient, the electrode is readily converted to its second or "open" configuration whereby the layer of conductive adhesive is exposed for contacting and adhering the bioelectrode to the body of the patient.

These two configurations are most conveniently provided by folding the backing into a self-sealing pouch. The generally flat backing has two surfaces: (1) the surface that is going to be inside the enclosure facing the conductive layer and the conductive adhesive, called the "inside surface", and (2) the surface which is going to be outside the enclosure, called the "outside surface". Near the edge of the inside surface of the backing is a peripheral portion. When the bioelectrode is folded, one region of this peripheral portion is placed in contact with another region of the peripheral portion. When one such region is sealed against the other, the sealed protective enclosure is made.

In preferred embodiments, the bioelectrode has an axis of substantial symmetry, and when the bioelectrode is in its first configuration the backing is folded along that axis. When the bioelectrode is a dispersive electrode intended to transfer current for electrosurgery, it is often convenient to provide the conductive layer as two separate conductive portions, since that adapts the bioelectode for use with "CQM"-type (for "Contact Quality Monitoring") generators. Then when the bioelectrode is in its first configuration the two conductive portions are on opposite sides of the fold axis.

For the physician to be able convert the bioelectrode to its second, "open" configuration, the seal between the two regions of the peripheral portions must be readily openable. One convenient way of providing this is to seal the two regions with a releasable adhesive. In other embodiments, the peripheral portion of the backing is severable from the rest of the backing. This is conveniently done by scoring or perforating.

In the second aspect, the invention provides a method of preparing a bioelectrode for shipping and handling prior to use, comprising the steps of providing a bioelectrode comprising a backing; a conductive layer adjacent to the backing; and a layer of conductive adhesive adjacent to the conductive layer; and folding the bioelectrode so as to form a sealed protective enclosure for the layer of conductive adhesive. In preferred embodiments, the backing has a first side which is adjacent to the conductive layer, that first side having a peripheral portion each having a first and second regions. The bioelectrode is folded so that one region of the peripheral portion is sealed against the other region, creating the sealed protective enclosure.

BRIEF DESCRIPTION OF THE DRAWING

The present invention will be further described with reference to the accompanying drawing wherein like reference numerals refer to like parts in the several views, and wherein:

FIG. 1 is plan view according to one presently preferred embodiment of the bioelectrode of the present invention in a first configuration;

FIG. 2 is a perspective view of the bioelectrode of FIG. 1 after having been unsealed;

DETAILED DESCRIPTION

Figure 3:
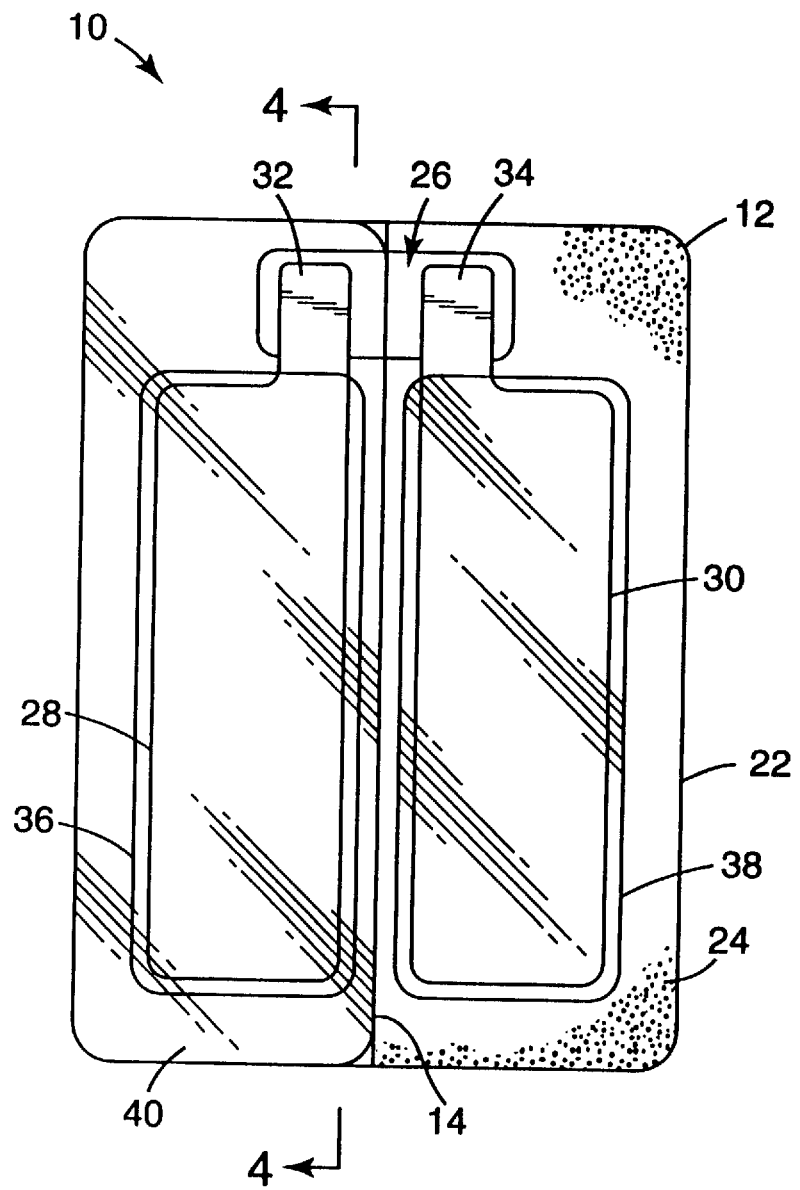
FIG. 3 is a bottom plan view of the bioelectrode of FIG. 2 after having been unfolded into a configuration.

Referring now to FIGS. 1 and 2, a top perspective view of bioelectrode 10 according to the present invention in a first configuration is illustrated. In this view, one half of the backing 12 is seen, backing 12 being folded over on itself along fold line 14. The backing 12 has a peripheral portion 16, of which a first region 18 is in view, and a second region 20 is on the far side of the view. In this embodiment, the peripheral portion 16 includes a score line 22. In FIG. 2, the peripheral portion 16 has been detached by the physician by tearing along the score line 22. The peripheral portion 16 is of no further use and is discarded; its small volume adds little to the waste stream of the hospital.

Referring now to FIG. 3, a bottom plan view of the bioelectrode 10 of FIG. 2 after having been unfolded into its second configuration is illustrated. Placing the bioelectrode 10 in this configuration is accomplished by unfolding the bioelectrode 10 along fold line 14. The parts of the bioelectrode 10 which were folded towards the inside in FIGS. 1 and 2 can now be seen in FIG. 3. The interior surface of backing 12 has been coated with a field of skin adhesive 24, except in region 26. The skin adhesive 24 holds a pair of conductive plates 28 and 30 to the backing 12. A pair of conductive tabs 32 and 34 extend from one end of the conductive plates 28 and 30, and these conductive tabs serve to connect the bioelectrode to e.g. an electrosurgical generator. Because the conductive tabs 32 and 34 extend into the region 26, they are free to lift away from the backing somewhat and be available for connection.

Two fields 36 and 38 of conductive adhesive are coated on top of the conductive plates 28 and 30 and serve to transfer the current from electrosurgical procedures from the body of the patient. Many compositions suitable for use for the two fields 36 and 38 of conductive adhesive are transparent, or at least translucent, and have been depicted that way for convenience in providing an explanatory drawing. It will be noted that the skin adhesive and the conductive adhesive on the two halves of the backing 12 will face each other when the bioelectrode 10 is folded. Some adhesives that can be used do not adhere significantly to themselves and are readily peeled from each other when the bioelectrode 10 is unfolded. Other useful adhesives cannot readily be peeled from each other, and need to be protected when the bioelectrode is in its folded condition. When these adhesives are in use, an internal liner 40 which is non-adhesive on both of its surfaces to both the skin adhesive and the conductive adhesive can be used to keep the layers on the two halves of the bioelectrode 10 apart in a manner analogous to a bookmark in a book keeping the facing pages apart. In FIG. 3, the internal liner 40 has been depicted as transparent for convenience in providing an explanatory drawing.

Figure 4:
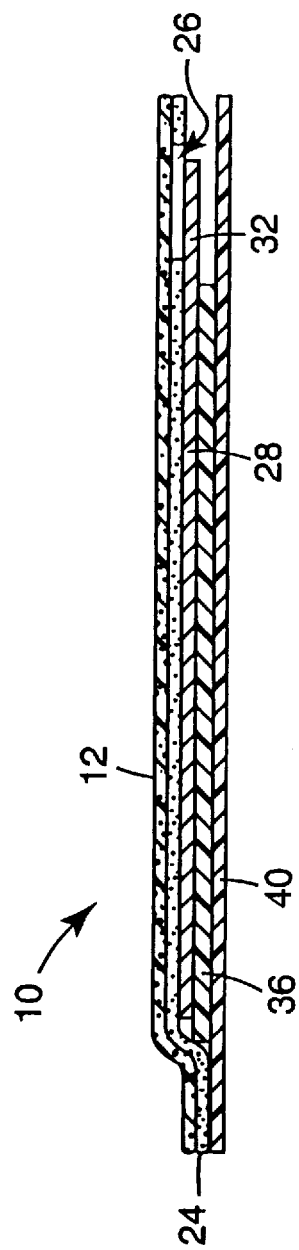
FIG. 4 is a cross-section view taken along section lines 4—4 in FIG. 3.

Referring now to FIG. 4, a cross-sectional view of bioelectrode 10, taken along section lines 4—4 in FIG. 3, is illustrated. Internal liner 40 is seen as still being adhered to the depicted half of bioelectrode 10. The internal liner 40 is peeled from the rest of the bioelectrode and discarded before use.

Backing

Backing 12 can be electrically insulative, and preferably is very conformable to the human body. Many material may be used for this purpose, as will be apparent to those skilled in the art. In one presently preferred embodiment, a closed-cell foam is considered particularly suitable; one such material is commercially available as Volara foam from Voltek, Inc. of Massachusetts. The backing has a thickness ranging from about 0.75 mm (0.03 inch) to about 1.5 mm (0.06 inch), and preferably 1.0 mm (0.04 inch).

Conductive layer

For the depicted application as a dispersive electrode for electrosurgery, the conductive layer of the bioelectrode is conveniently made from thin aluminum laminated to polyethylene terephthalate (PET) film. The PET film is conveniently approximately 0.05 mm (0.002 inch) thick, and the aluminum layer conveniently ranges in thickness between about 0.0075 mm (0.0003 inch) to about 0.025 mm (0.001 inch) and preferably 0.012 mm (0.0005 inch). For diagnostic applications, where non-polarizability is a consideration, the conductive layer is conveniently formed from an electrically non-conductive sheet of plastic coated with silver/silver chloride on the surface adjacent the conductive adhesive. Such a coating is conveniently accomplished by use of a silver/silver chloride ink; one suitable ink is commercially available as R-301 from Ercon of Waltham, Mass. Alternatively, the conductive layer can be constructed from materials disclosed in PCT publications WO 94/26950 and WO 95/20350, the disclosures of which are incorporated herein by reference. As a further alternative, the conductive layer can be constructed from graphite materials as disclosed in U.S. Pat. No. 5,215,087.

Conductive adhesive

Nonlimiting examples of conductive adhesives useful in connection with the present invention include those compositions disclosed in U.S. Pat. Nos. 4,524,087 (Engel); 4,539,996 (Engel); 4,848,353 (Engel); 5,225,473 (Duan); 5,276,079 (Duan et al); 5,338,490 (Dietz et al); 5,362,420 (Itoh et al); 5,385,679 (Uy et al); 5,133,356 (Bryan et al); copending and coassigned applications PCT Publication Nos. WO 95/20634 and WO 94/12585; and U.S. patent application Ser. Nos. 95/17079; 95/16993; and 95/16996, the disclosures of which are incorporated by reference herein.

Internal liner

Internal liner 40 can be any construction suitable for protecting the conductive adhesive and/or the skin adhesive from adhering to itself when the bioelectrode 10 is in its first configuration. One suitable liner is a 0.05 mm (0.002 inch) thick sheet of biaxially oriented polypropylene liner, commercially available as Daubert 1-2 BOPPL-164Z from Daubert Co. of Dixon, Ill.

Skin adhesive

Nonlimiting examples of skin adhesives 24 useful in connection with the present invention include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all incorporated herein by reference.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A bioelectrode, comprising:

a backing;

a conductive layer adjacent to the backing; and a layer of conductive adhesive adjacent to the conductive layer; wherein the bioelectrode is placed in a first configuration wherein the backing forms a sealed protective enclosure for the layer of conductive adhesive, and is adapted to have a second configuration wherein the layer of conductive adhesive is exposed for use in contacting the body of a patient.

2. The bioelectrode according to claim 1 wherein the backing has a first side which is adjacent to the conductive layer, that first side having a peripheral portion first and second regions; and further wherein when the bioelectrode is in its first configuration, the backing is folded upon itself so that one region of the peripheral portion is sealed against the other region, creating the sealed protective enclosure.

3. The bioelectrode according to claim 2 wherein the bioelectrode has an axis of substantial symmetry, and further wherein when the bioelectrode is in its first configuration the backing is folded along that axis.

4. The bioelectrode according to claim 3 wherein the conductive layer comprises two separate conductive portions, such that when the bioelectrode is in its first configuration the two conductive portions are on opposite sides of the axis.

5. The bioelectrode according to claim 2 wherein when the bioelectrode is in its first configuration, the first and second regions are sealed one to another with a releasable adhesive.

6. The bioelectrode according to claim 2 wherein when the bioelectrode is in its first configuration, the first and second regions are sealed one to another with a non-releasable adhesive, and further wherein the peripheral portion of the backing is adapted to be severed from the rest of the backing.

7. The bioelectrode according to claim 4, wherein layer of conductive adhesive comprises two separate fields of conductive adhesive and wherein the bioelectrode further comprises an internal liner, such that when the bioelectrode is in its first configuration, the internal liner separates the fields of conductive adhesive.

8. A method of preparing a bioelectrode for shipping and handling prior to use, comprising the steps of:

providing a bioelectrode comprising a backing; a conductive layer adjacent to the backing; and a layer of conductive adhesive adjacent to the conductive layer; and folding the bioelectrode so as to form a sealed protective enclosure for the layer of conductive adhesive.

9. The method according to claim 8 wherein the backing has a first side which is adjacent to the conductive layer, that first side having a peripheral portion first and second regions; and further wherein the bioelectrode is folded so that one region of the peripheral portion is sealed against the other region, creating the sealed protective enclosure.

10. The method according to claim 9 wherein the bioelectrode has an axis of substantial symmetry, and further wherein when the bioelectrode is folded along that axis.

11. The method according to claim 9 wherein the conductive layer comprises two separate conductive portions, such that when the bioelectrode is folded the two conductive portions are on opposite sides of the axis.

12. The method according to claim 9 wherein when the bioelectrode is folded the first and second regions are sealed one to another with a releasable adhesive.

13. The method according to claim 9 wherein when the bioelectrode is folded the first and second regions are sealed one to another with a non-releasable adhesive, and further wherein the peripheral portion of the backing is adapted to be severed from the rest of the backing.

14. The method according to claim 11, wherein the layer of conductive adhesive comprises two separate fields of conductive adhesive and wherein the method further comprises placing an internal liner adjacent one of the fields of conductive adhesive before the folding step.

* * * * *